US010137268B2

(12) United States Patent
Reinberg

(10) Patent No.: US 10,137,268 B2
(45) Date of Patent: Nov. 27, 2018

(54) SYSTEM AND METHOD FOR SECURING A BREATHING GAS DELIVERY HOSE

(71) Applicant: Richard D. Reinberg, Beachwood, OH (US)

(72) Inventor: Richard D. Reinberg, Beachwood, OH (US)

(73) Assignee: CPAP Miracle LLC, Beachwood, OH (US)

( * ) Notice: Subject to any disclaimer, the term of this patent is extended or adjusted under 35 U.S.C. 154(b) by 0 days.

(21) Appl. No.: 15/895,680

(22) Filed: Feb. 13, 2018

(65) Prior Publication Data

US 2018/0200466 A1 Jul. 19, 2018

Related U.S. Application Data

(63) Continuation-in-part of application No. 15/360,003, filed on Nov. 23, 2016, now abandoned, which is a continuation-in-part of application No. 14/851,832, filed on Sep. 11, 2015, now abandoned, and a continuation-in-part of application No. 29/632,847, filed on Jan. 10, 2018, now Pat. No. Des. 820,443.

(60) Provisional application No. 62/051,981, filed on Sep. 18, 2014.

(51) Int. Cl.
| | |
|---|---|
| *A61M 16/04* | (2006.01) |
| *F16C 11/12* | (2006.01) |
| *F16M 11/20* | (2006.01) |
| *A61M 16/08* | (2006.01) |

(52) U.S. Cl.
CPC .... *A61M 16/0497* (2013.01); *A61M 16/0816* (2013.01); *A61M 16/0875* (2013.01); *F16C 11/12* (2013.01); *F16M 11/2014* (2013.01); *F16M 11/2057* (2013.01); *A61M 2209/082* (2013.01)

(58) Field of Classification Search
CPC .. F16L 3/13; A61M 16/0497; A61M 16/0816; A61M 2209/082; A61M 16/0875; F16C 11/12; F16M 11/2014; F16M 11/2021; F16M 11/2057
USPC .... 248/80, 75, 161, 160; 403/229, 220, 223, 403/221, 291; 267/168; 464/78
See application file for complete search history.

(56) References Cited

U.S. PATENT DOCUMENTS

| | | | | | |
|---|---|---|---|---|---|
| 1,557,958 | A | * | 10/1925 | Anderson | F16D 3/72 279/16 |
| 1,774,742 | A | * | 9/1930 | Ash | H02G 11/003 248/160 |
| 1,890,696 | A | * | 12/1932 | Rosenhahn | A63B 69/208 248/160 |
| 2,890,799 | A | * | 6/1959 | Rosenbaum | A47H 1/08 16/87.4 R |
| 3,150,506 | A | * | 9/1964 | Alcaro | F16D 3/72 464/78 |
| 3,543,599 | A | * | 12/1970 | Caswell | B64C 13/02 244/234 |

(Continued)

*Primary Examiner* — Christopher Garft
(74) *Attorney, Agent, or Firm* — Ulmer & Berne LLP

(57) ABSTRACT

A system and method for supporting a patient gas delivery tube includes an elongated support member having first and second distal end and a living hinge biasing arcuate movement between the distal ends. A generally planar, rigid base configured to secures a lower distal end so that the support member extends from a surface of the base. A mount secured to the other distal end is adapted to secure an associated tube.

6 Claims, 9 Drawing Sheets

(56) References Cited

U.S. PATENT DOCUMENTS

| | | | | |
|---|---|---|---|---|
| 3,999,730 | A * | 12/1976 | Gonsalves | E01B 25/26 246/434 |
| 5,263,594 | A * | 11/1993 | Bianchi | A47H 1/06 16/96 R |
| 5,741,429 | A * | 4/1998 | Donadio, III | A61M 25/0043 216/10 |
| 6,203,437 | B1 * | 3/2001 | Durie | F16D 3/72 403/220 |
| 6,749,560 | B1 * | 6/2004 | Konstorum | A61B 1/00071 600/139 |
| 8,979,739 | B2 * | 3/2015 | Seto | A61M 25/0138 600/139 |
| 2006/0276247 | A1 * | 12/2006 | Martinez | F16C 1/02 464/78 |
| 2007/0045481 | A1 * | 3/2007 | Adams | A61G 7/0503 248/59 |
| 2008/0077119 | A1 * | 3/2008 | Snyder | A61M 25/0051 604/525 |
| 2008/0236588 | A1 * | 10/2008 | Livingston | A61M 16/06 128/205.25 |
| 2009/0039210 | A1 * | 2/2009 | Yates | F16L 3/1218 248/74.1 |
| 2012/0158004 | A1 * | 6/2012 | Burger | A61B 17/8811 606/94 |
| 2017/0095138 | A1 * | 4/2017 | Nakade | G02B 23/24 |
| 2017/0203072 | A1 * | 7/2017 | Tonning | A61G 12/002 |

* cited by examiner

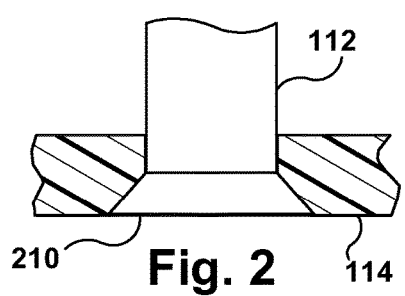
Fig. 2
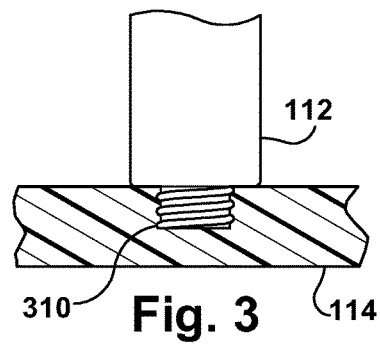
Fig. 3
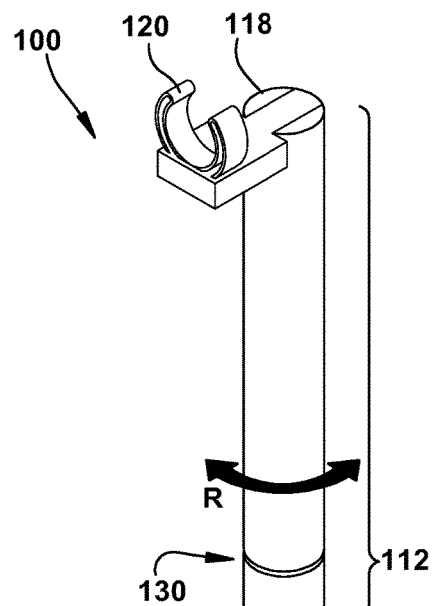
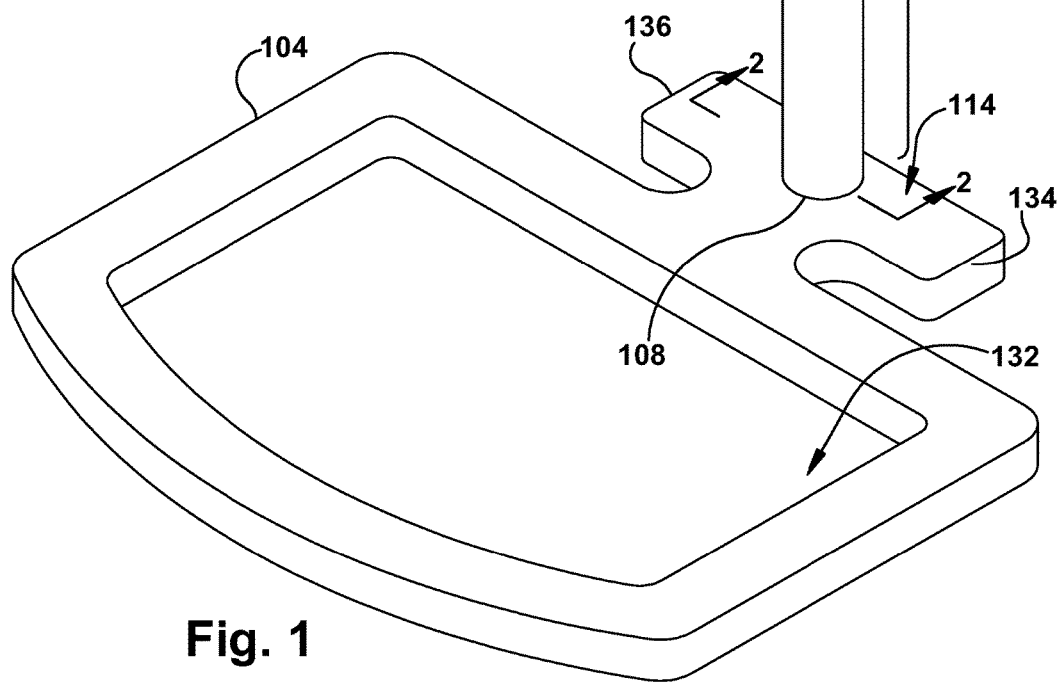
Fig. 1

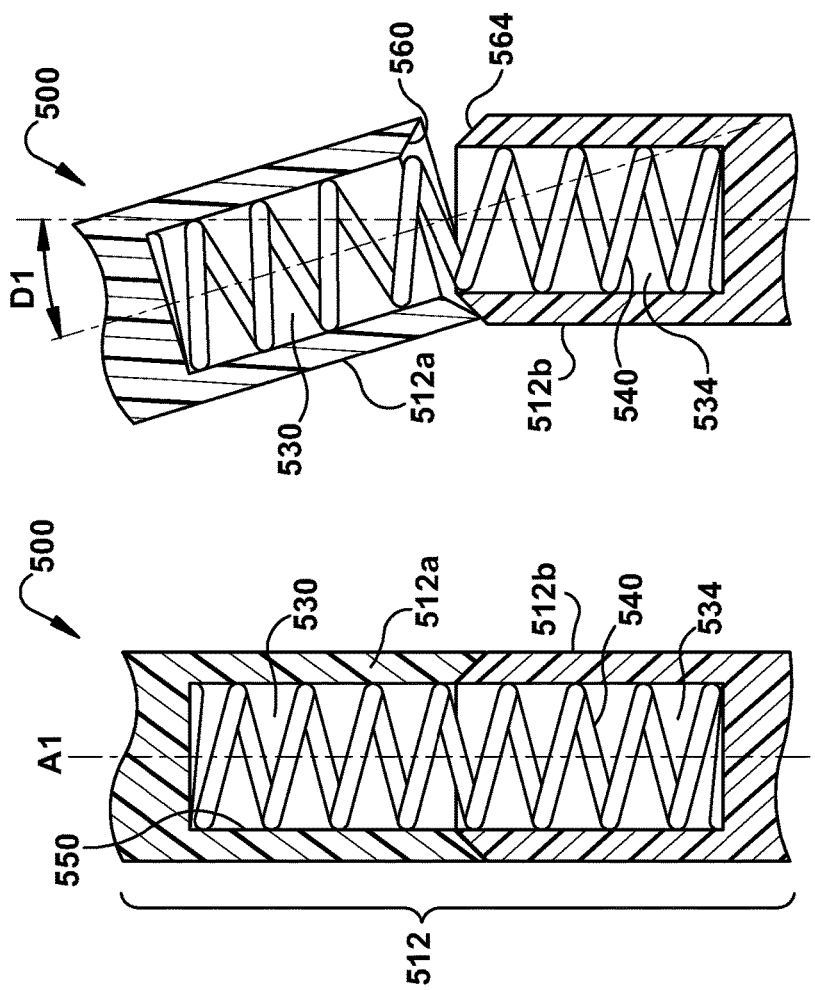

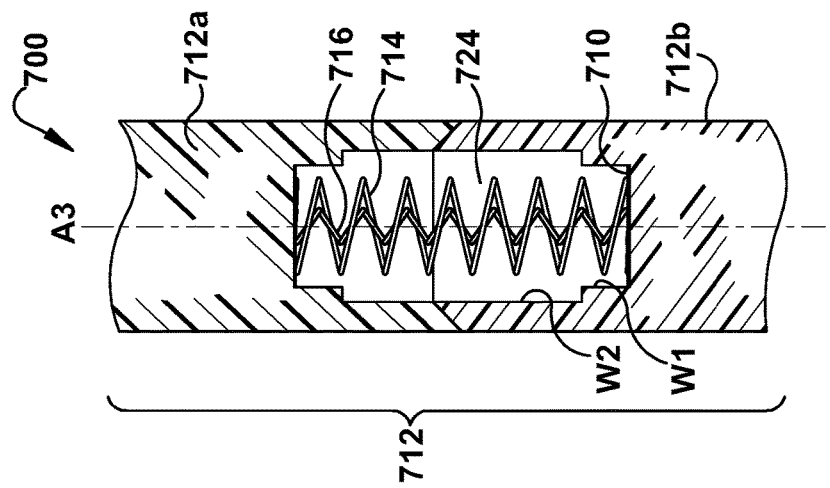
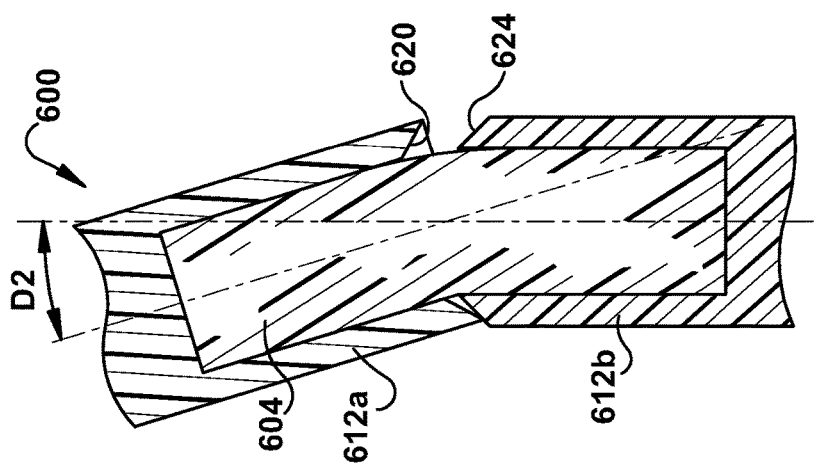
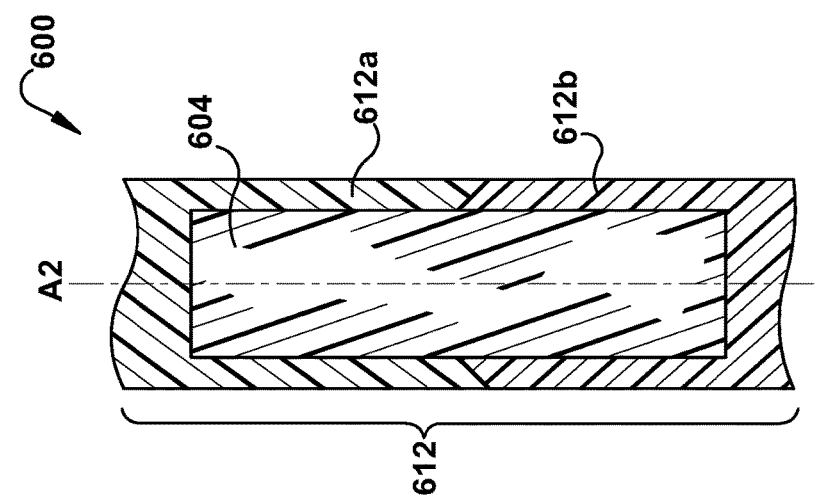
Fig. 7
Fig. 6B
Fig. 6A

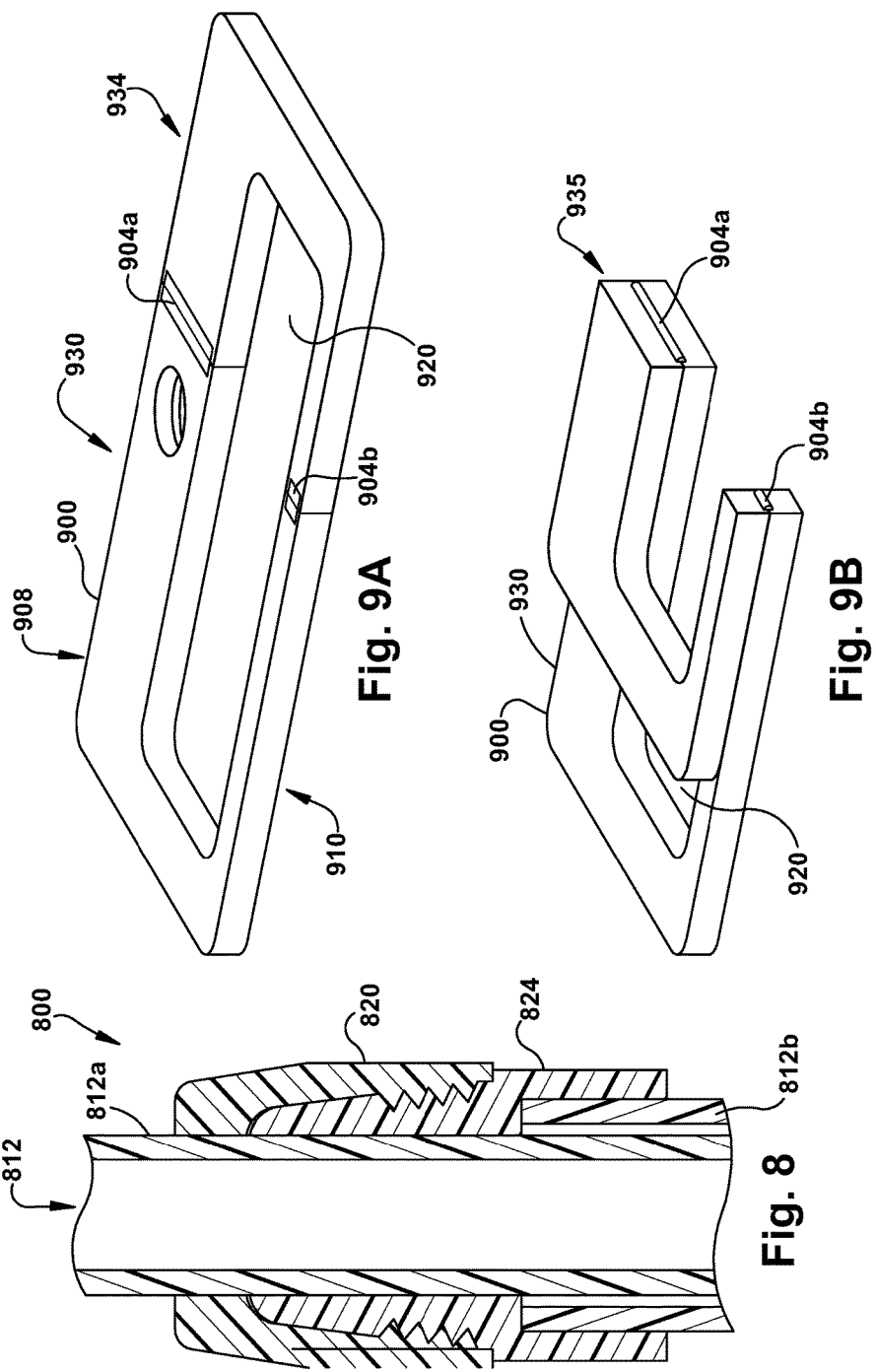

SYSTEM AND METHOD FOR SECURING A BREATHING GAS DELIVERY HOSE

REFERENCE TO RELATED APPLICATIONS

This application is a continuation-in-part to U.S. patent application Ser. No. 15/360,003, filed Nov. 23, 2016, which is a continuation-in-part of U.S. patent application Ser. No. 14/851,832 filed Sep. 11, 2015 which claims the benefit of U.S. Provisional Patent Application No. 62/051,981 filed Sep. 18, 2014, all of which are herein incorporated by reference. This application is also a continuation in part to U.S. Design patent application Ser. No. 29/632,847 filed Jan. 10, 2018, the content of which is also incorporated herein by reference.

TECHNICAL FIELD

This application relates generally to securing flexible tubing. The application relates more particularly to securing breathing gas tubing while supplying gas to the facial area of a sleeping person.

BACKGROUND

Breathing, also known as respiration, includes a cycle if inhalation and exhalation. A rate at which breaths occur is usually measured in breaths per minute. A typical adult human has a breathing or respiratory rate of 12-20 breaths per minute, but what is typical varies by age, degree of physical exertion and overall health and physiology of human individuals. By way of example, a newborn baby may take 30-40 breaths per minute, while a septuagenarian may only take 12-28 breaths per minute.

One of the more common breathing conditions is apnea, defined as a temporary cessation of breathing. Apnea can be voluntarily achieved by holding one's breath. Apnea can also be drug-induced, such as by opiate toxicity or tryptamine toxicity; mechanically induced by strangulation or choking; as a consequence of neurological disease or trauma; or by strong emotional episodes, such as laughing or crying. During apnea, there is no significant movement of muscles used during inhalation.

Sleep apnea is a potentially serious sleep disorder in which breathing repeatedly stops and starts. One may have sleep apnea if they snore loudly or feel tired even after a full night's sleep. The main types of sleep apnea are: obstructive sleep apnea, the more common form that occurs when throat muscles relax; central sleep apnea, which occurs when your brain doesn't send proper signals to the muscles that control breathing; and complex sleep apnea syndrome, also known as treatment-emergent central sleep apnea, occurs when someone has both obstructive sleep apnea and central sleep apnea. Risks from sleep apnea include high blood pressure, stroke, heart failure, irregular heartbeat, and heart attacks.

One successful way to treat sleep apnea is continuous positive airway pressure, or CPAP (pronounced "see-pap"). This treatment uses mild air pressure to keep the airways open. This is accomplished by sealing a mask over a patient's airway with the mask supplying positive pressure by gas delivered to the mask from a pump or reservoir via a delivery tube or hose. While a patient may become accustomed to wearing a mask at night, they must always contend with the associated gas delivery hose, particularly as they toss or turn during sleep.

SUMMARY

In accordance with an example embodiment of the subject application, a system and method for supporting a patient gas delivery tube includes an elongated support member having first and second distal end and a living hinge biasing arcuate movement between the distal ends. A generally planar, rigid base configured to secures a lower distal end so that the support member extends from a surface of the base. A mount secured to the other distal end is adapted to secure an associated tube.

BRIEF DESCRIPTION OF THE DRAWINGS

Various embodiments will become better understood with regard to the following description, appended claims and accompanying drawings wherein:

FIG. 1 is an example embodiment of a gas delivery hose support;

FIG. 2 is a first example embodiment of a fastening of a support member;

FIG. 3 is a second example embodiment of a fastening of a support member;

FIG. 5A is a first example embodiment of a biasing portion of a support member;

FIG. 5B is a second view of the example embodiment of a biasing portion of a support member in FIG. 5A;

FIG. 6A is a second example embodiment of a biasing portion of a support member;

FIG. 6B is a second view of the example embodiment of a biasing portion of a support member in FIG. 6A;

FIG. 7 is a third example embodiment of a biasing portion of a support member;

FIG. 8 is an example embodiment of a telescoping joint;

FIG. 9A is an example embodiment of a hinged base portion;

FIG. 9B is an example embodiment of the hinged base portion of FIG. 9A;

DETAILED DESCRIPTION

Figure 4C:
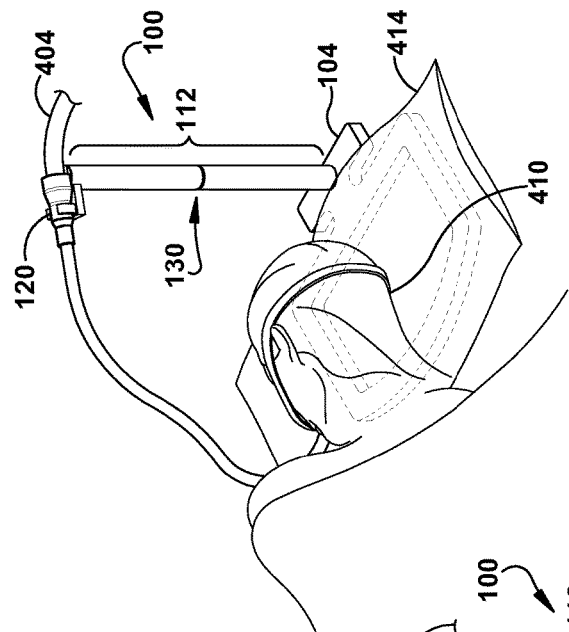
FIG. 4C is a third view of an example use of a gas delivery hose support by a human of FIG. 4A.

The systems and methods disclosed herein are described in detail by way of examples and with reference to the figures. It will be appreciated that modifications to disclosed and described examples, arrangements, configurations, components, elements, apparatuses, devices methods, systems, etc. can suitably be made and may be desired for a specific application. In this disclosure, any identification of specific techniques, arrangements, etc. are either related to a specific example presented or are merely a general description of such a technique, arrangement, etc. Identifications of specific details or examples are not intended to be, and should not be, construed as mandatory or limiting unless specifically designated as such.

In accordance with the subject application, FIG. 1 illustrates an example embodiment of a gas delivery hose support 100. Included is a generally planar, rigid base 104 configured to receive and support lower distal end 108 of an elongated support member 112 at a surface 114. Support member 112 is suitably fastened to base 104 by any suitable means, such as a threaded connector, snap connector or slip connector as will be understood by one of ordinary skill in the art. Further example embodiments will be detailed below. As will also be detailed below, example embodiments herein provide for relative angular movement between lower distal end 108 and upper distal end 118 of support member 112, illustrated as a biased C-clamp 120, which is configured to receive and secure an associated gas delivery hose or tube 116 and configured to flex when a hose is inserted or removed. The hose is, in turn, connected to a gas reservoir, such as an air or oxygen cylinder, or a pump, such as an air pump, so as to provide a continuous flow of gas to an associated CPAP mask on an associated user.

As will be detailed further below, angular movement between upper distal end 118 and lower distal end 108 allows for accommodation of movement of sleeping persons who are wearing a CPAP mask which is connected to a hose (note shown) at connector 120. In an embodiment, angular movement between distal ends allows for side-to-side movement of connector 120, thereby providing freedom of movement to a sleeping user while suspending the breathing hose above them. Biasing provides for a return to resting position of support member 112, for example return to a center rotational position or return to a vertical position of the support member 112. Biasing is suitably accomplished by a resilient construction of support member 112, or by a biased pivot or hinge portion 130 between the distal ends as will be further detailed below. Pivot or hinge portion 130 is also suitably enabled for axial rotation R to permit further freedom of movement to an associated gas delivery hose or tube 116 connected at connector 120.

Base 104, as well as all or some of support member 112, are suitably constructed from any rigid material, such as plastic, metal or wood. In certain embodiments, plastic may be more desirable given its relatively low cost and weight. In other embodiments, a medical grade composition, such as bacteria-resistant plastic, may be suitable, such as in clinical or hospital environments.

FIGS. 2 and 3 show example embodiments of a fastening of support member 112 to base 104 along cut line 2-2 of FIG. 1. In the example embodiment of FIG. 2, connection is made with a flange 210 while in the example embodiment of FIG. 3, connection is made with a threaded connection 310.

In the example embodiment of FIG. 1, base 104 includes an opening or ring area 132 which provides for a relatively high moment of inertial relative to elongated member 112 by virtue of base dimensions while minimizing weight and construction material cost. Base projection 138 extends outward from ring area 132 and is positioned so as to project outside a pillow edge when ring area 132 is disposed under a pillow. First and second projections 134 add further angular rigidity relative to support 112.

In the example embodiment of FIG. 1, base 104 includes an opening or ring area 132 which provides for a relatively high moment of inertial relative to elongated member 118 by virtue of base dimensions while minimizing weight and construction material cost. Base projections 134, 136 extends outward from ring area 133 and is positioned so as to project outside a pillow edge when ring area 130 is disposed under a pillow. First base projection 134 and second projection 136 add further angular rigidity relative to support 112. Base 104 is constructed so as to be readily place able under a sleeping area, such as under a pillow or under a mattress where it will be relatively immobile relative to a sleeping user. In a configuration, having a relatively short support member 112 advantageously allows for use of less material and provides a unit that is smaller, and thus more transportable, than a floor-supported base unit. Furthermore, when support member 112 is selectively removable from base 104, the gas delivery host support 100 is rendered even more compact for transporting, such as in a user's suitcase.

Figure 4B:
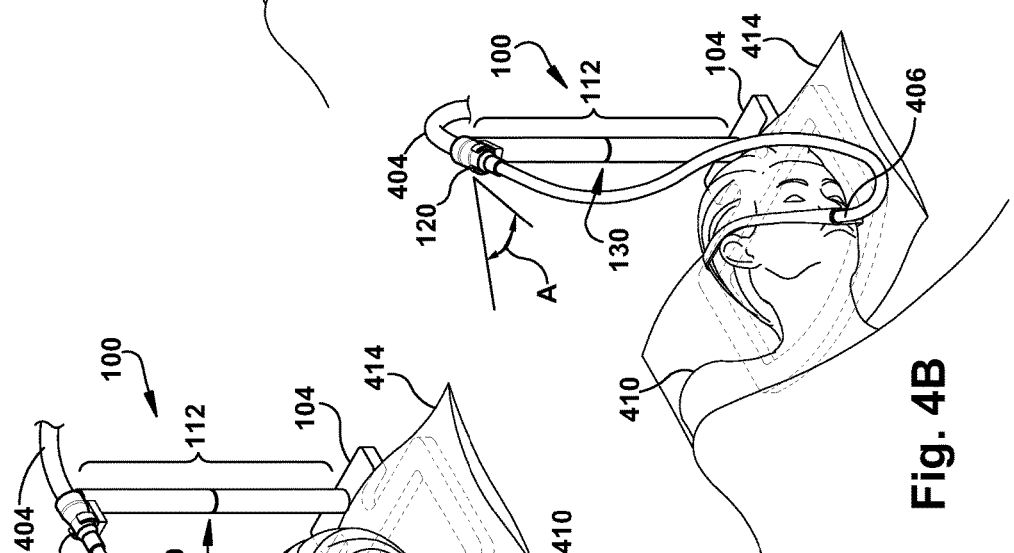
FIG. 4B is a second view of an example use of a gas delivery hose support by a human of FIG. 4A.
Figure 4A:
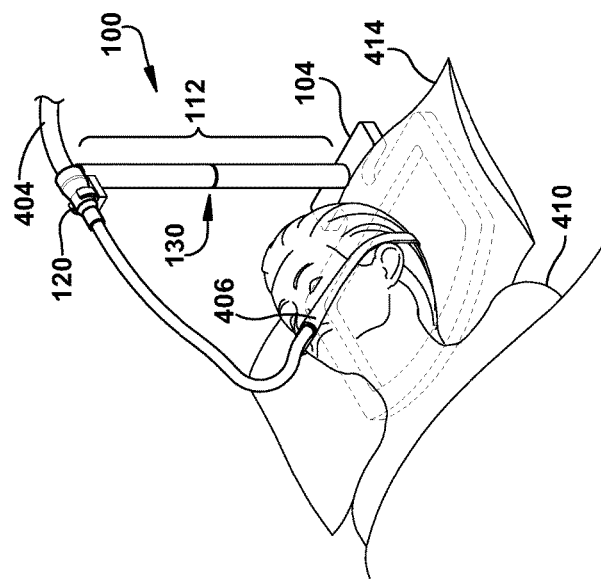
FIG. 4A is a first view of an example use of a gas delivery hose support by a human.

FIGS. 4A-4C illustrate example use by a human of the gas delivery hose support 100 of FIG. 1. Hose 404 is connected hose support 100 at connector 120 and supplies CPAP device 406 with pressurized gas. CPAP device 406 is provided to one or more breathing orifices of human user 410. In FIG. 4A, user 410 is in a resting position on pillow 414 which is, in turn, disposed over base 104 of the gas delivery hose support 100. FIG. 4B illustrates an example of rotation of connector 120 via biased pivot or hinge portion 130 during user movement as illustrated by angle A. FIG. 4C similarly illustrates user movement in the opposite direction.

FIGS. 5A and 5B illustrate a cut away view of an example embodiment of a biasing area 500 of a hose support such as hose support 100 of FIG. 1. In the illustrated example embodiment, support member 512 is comprised of support member portion 512a and support member portion 512b. Portions 512a and 512b are suitably coaxial along axis A1 and cylindric in cross section, such as having an oval or circular cross section. Portions 512a and 512b intersect at a biasing portion 220 engineered to permit flexing between the portions at an angle D1. Biasing portion 520 is suitably comprised of a first hollowed out portion 530 at a distal end of portion 512a and a second hollowed out portion 534 at a distal end of portion 512b. A biasing member 540, such as a spring, is disposed in the hollowed out portions 530 and 534 to maintain both portions 512a and 512b generally in coaxial alignment. In the illustrated example, spring 540 is disposed so as to be closely proximate to internal side wall 550 formed from hollowed out portions 530 and 534. When support member portions 512a and 512b, hollowed out portions 530 and 534 and biasing member 540, are oriented coaxially as illustrated, angular movement between distal ends of portions 512a and 512b is enabled with relative deflection being a function of angular force being applied at the distal ends and biasing properties of the biasing member 540. In the event of a spring biasing member, opposing force, tending to return the support member portions 512a and 512b to coaxial alignment, is a function of spring properties, including diameter, coil density and spring constant.

With the biasing portion 520 constructed as detailed above, a hose secured at a distal end of an associated hose support is enabled to move relative to a generally fixed base securing. When the hose extends to a face of a CPAP user, the hose will be suspended above them so as preclude rolling on to the hose while sleeping. The hose will be urged to return to rest on an upright support member by operation of biasing portion 520. Spring properties are suitably chosen to provide greater counter force to angular movement between portions 512a and 512b as greater angular deflection between the portions is realized. Thus, a sleeping user will be subtly urged to return toward a central position relative to the hose holder after turning one way or the other.

In the illustrated example embodiment of FIG. 5B, adjoining ends 560 and 564 of support member portions 512*a* and 512*b*, respectively, are comprised of complementary frustoconical portions, suitably matingly engaged when the support member portions 512*a* and 512*b* are disposed coaxially. This complementary mating engagement facilitates angular displacement between the support member portions 512*a* and 512*b* while maintain general coaxial alignment between the support member portions 512*a* and 512*b* during a pivot between them, thus keeping the support member portions 512*a* and 512*b* from separating completely and function to realign along axis A1 when urged to the coaxial position by the biasing portion 520.

In the illustrated example of FIG. 5A/B, hose support can be assembled/disassembled for transportation or storage by separating support portions 512*a* and 512*b*. In a more particular example, a spring 540 is suitably placed in hollowed out portion 530 and hollowed out portion 534 during assembly, or alternatively fixed in an interior of one portion and removably placeable into the other.

Referring next to FIGS. 6A and 6B, illustrated is an example embodiment of a biasing area 600 suitably implemented in connection with a support member such as detailed above. Flexible member 604 is disposed between a hollowed out portion of upper support member portion 612*a* and hollowed out portion of lower support member portion 612*b* having generally the same radial dimensions as upper support member portion 308. Upper support member portion 612*a* can include a concave bevel portion 620 at a lower distal end thereof. Lower support member portion 612*b* can include a convex bevel portion 624 at an upper distal end thereof. When a corresponding CPAP support unit is assembled, the lower distal portion is disposed end-to-end with upper distal portion such that complementary bevel portions are matingly engaged and enabled to pivot against one another while an opposing force is supplied by spring member 604 to angular displacement D2 relative to axis A2. Flexible member 604 can be suitably affixed to one of upper support member portion 612*a* or lower support member portion 612*b* to permit ease in assembly or disassembly of the two portions, or alternatively placed in the hollowed out areas of both portions during assembly. In various embodiments, flexible member can be any suitable flexible material including such non-limiting examples as a flexible rubber, a flexible plastic, a flexible polymer, a flexible composition, a flexible solid plug, a flexible tube, or other flexible materials or shapes as would be understood in the art. In various embodiments, the flexible member can be configured to be removable or fixed in one or both of the hollowed out portions of the support members.

Referring next to FIG. 7, illustrated is an example embodiment of a biasing area 700 suitably implemented in connection with a support member 712 having an upper portion 712*a* and lower portion 712*b*. In the illustrated example, a plurality of helical springs, illustrated by spring 714 and spring 716 are implemented and are generally coaxial along axis A3 and both secured to a bottom portion 720 of a hollowed out portion 724 of lower portion 712*b*. Spring 714 has a greater radial width than spring 716. Aggregate properties, including spring constants, lengths, coil widths and coil densities determine deflection counter forces. As will be understood by one of ordinary skill in the art, engineered biasing over various deflection points is thus enabled by selection of springs and spring properties for spring 714 and spring 716.

Also illustrated in the example of FIG. 7, hollowed out portion 724 suitably includes a plurality of internal diameter widths, such as w1 and w2. When springs 714 and 716 flex during a bending of support member 712, force properties will be altered when one or more springs encounters an internal wall of the hollowed out portion 724. Thus, lengths and widths of internal walls are suitably engineered to tune flexure properties as desired.

Referring next to FIG. 8, illustrated is an example embodiment of a telescoping joint 800 suitably implemented on support member 812, comprised of upper portion 812*a* and lower portion 812*b*. In the illustrated example, lower portion 812*b* has a greater radial diameter than upper portion 812*a* so as to allow nesting therebetween. Interaction between coaxial threaded portions 820 and 824 with support member portions 812*a* and 812*b* allows for selectively lengthening or shortening a length of support by loosening threaded member 820 relative to threaded member 824, adjusting relative position between the member portions, and then retightening the same.

FIGS. 9A and 9B illustrate another example embodiment of a base portion 900 in accordance with an extended position in FIG. 9A versus a folded position in FIG. 9B. A hinge portion 904, suitably comprised of two sections 904*a* and 904*b* when oriented to coincide with base opening 920. The hinge area is suitably disposed between first side 930 and second side 934 and is suitably implemented to allow for folding of base portion 900 to have a smaller surface area for packing in smaller suitcases, briefcases, carry-on baggage, and the like. In an embodiment, the hinge can be configured to inhibit collapsing during use. For example, the hinge can be disposed on the bottom surface of the base portion 900 such that the base must be lifted off of a surface before the base can be folded. Any suitable hinge or flexible member can be suitably implemented as will be understood by one of ordinary skill in the art.

Figure 10:
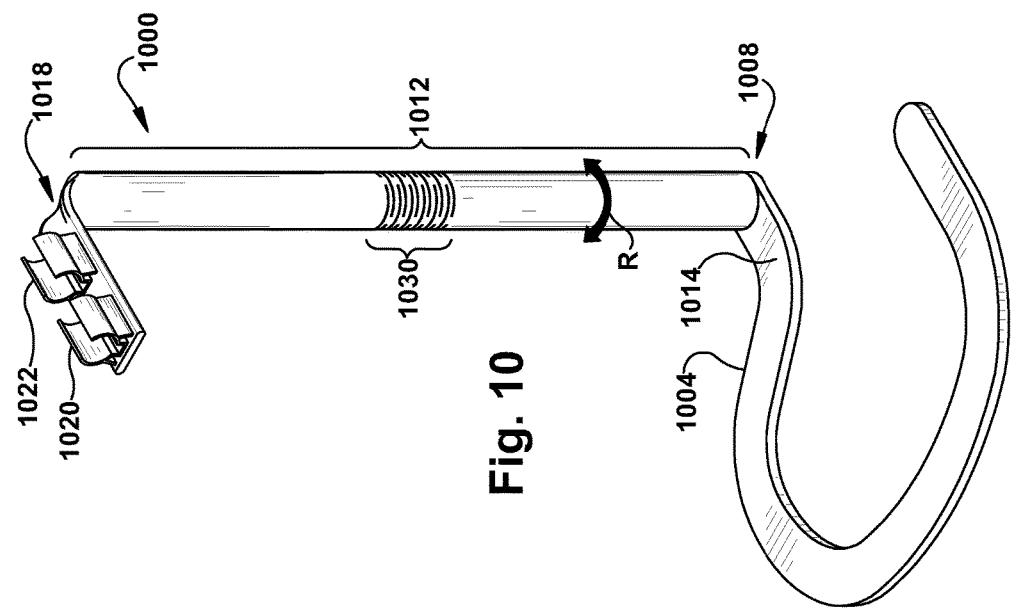
FIG. 10 is an example embodiment of a gas delivery hose support with a living hinge.

In accordance with the subject application, FIG. 10 illustrates an example embodiment of a gas delivery hose support 1000. Included is a generally planar, rigid base 1004 configured to receive and support lower distal end 1008 of an elongated support member 1012 at a surface 1014. Base 1004 is curvilinear so as to provide secure support to support member 1012 with minimal material when disposed under a pillow or mattress. Support member 1012 is suitably comprised of a semi rigid to rigid polymeric material such as polyvinyl chloride (PVC). In the illustrated embodiment, support member 1012 is comprised of a tube or pipe, but any suitable cross section, including oval polygon can be used. Support member 1012 is removeably and rotatably linked to base 1004 for rotational movement R as will be detailed further below. As will also be detailed below, example embodiments herein provide for relative angular movement between lower distal end 1008 and upper distal end 1018 of support member 1012. A hose fastener, illustrated as a biased C-clamp pair 1020 and 1022, is configured to receive and secure an associated gas delivery hose or tube at upper distal end 1018. C-Clamps 1020 and 1022 are configured to flex when a hose is inserted or removed. The hose is, in turn, connected to a gas reservoir, such as an air or oxygen cylinder, or a pump, such as an air pump, so as to provide a continuous flow of gas to an associated CPAP mask on an associated user. First and second C-clamps provide for a greater axial coverage area of a gas hose facilitating increased leverage for rotation of support member 1012, due to a person's movement with a breathing hose. A single, longer C-clamp is also suitable, but may require more effort to fasten or unfasten a hose due to larger springing surfaces.

Angular axial movement between upper distal end 1018 and lower distal end 1008 allows for accommodation of movement of sleeping persons who are wearing a CPAP mask which is connected to a hose (note shown) at connectors 1020 and 1022. In an embodiment, angular movement between distal ends allows for side-to-side movement of connectors 1020 and 1022, thereby providing freedom of movement to a sleeping user while suspending the breathing hose above them. Biasing provides for a return to resting position of support member 1012, for example return to a center rotational position or return to a vertical position of the support member 1012. Biasing is suitably accomplished by a resilient construction of support member area 1030 comprised of a living hinge. In the illustrated example, living hinge 1030 is comprised of a series of complementary cuts into a wall of support member 1012. It will be noted expanded that no cut extends completely through tube wall. When so constructed, living hinge provides flexure between lower distal end 1008 and upper distal end 1018. Spacing between cuts, depth of cuts and axial length of living hinge 1030, coupled with properties associated with a selected polymeric material, correspond to a spring constant for flexure. Controlling of one or all of these properties provides for a desired spring biasing, such as with setting a spring constant for living hinge 1030.

Figure 11:
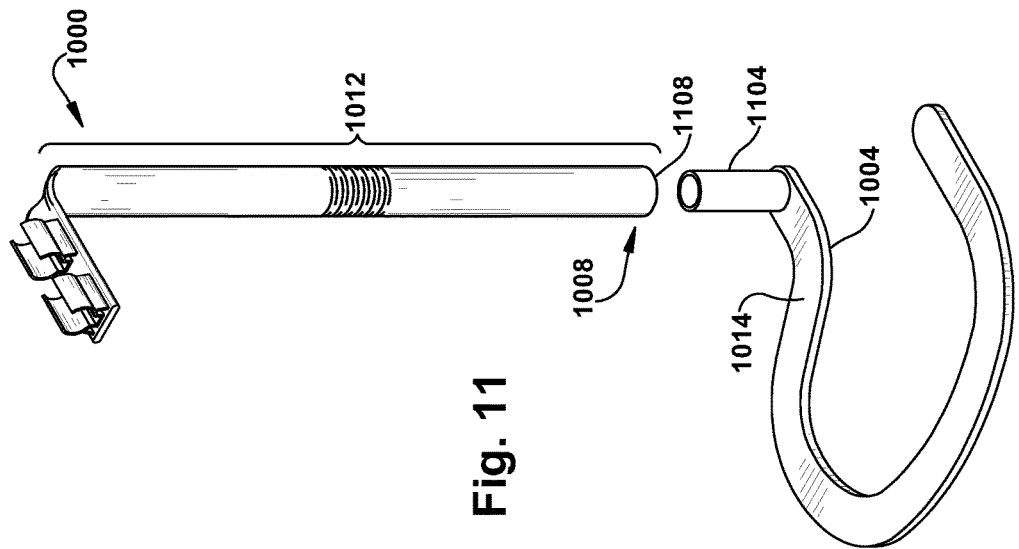
FIG. 11 is a second view of the example embodiment of a gas delivery hose support in FIG. 10 showing a removable base.

FIG. 11 is shows the delivery hose support 1000 of FIG. 10 with support member 1012 detached from base 1014. Support member 1012 is comprised of a polymeric tube adapted to be received on a cylindrical projection 1104 mounted generally perpendicularly to surface 1014 of base 1004. An exterior diameter of projection 1104 is selected for a slip fit into opening 1108 of lower distal portion 1008. This construction allows for disassembly of base 1004 from support member 1012 providing for packaging, stowing or travel, as well as freedom for rotational movement of support member 1012.

Figure 13:
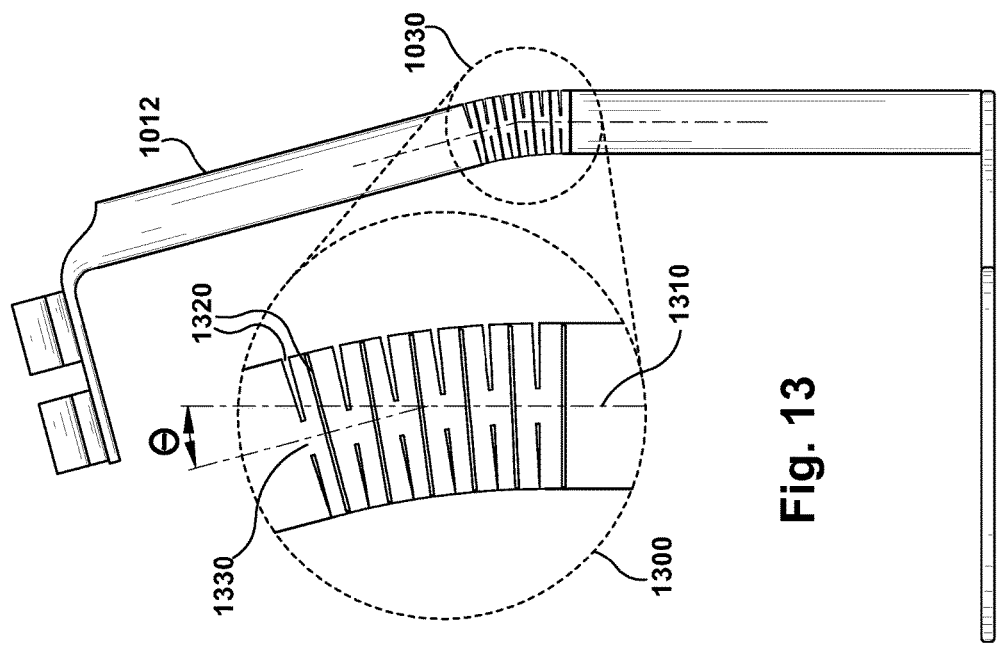
FIG. 13 is an example embodiment of a gas delivery hose support with a flexible, living hinge.
Figure 12:
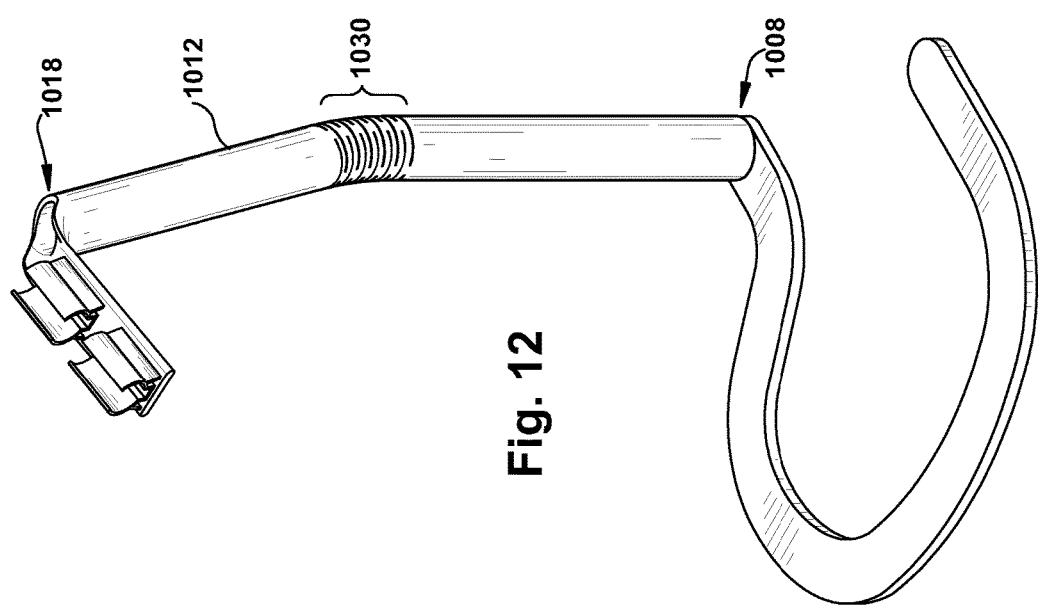
FIG. 12 is an example embodiment of the gas delivery hose support of FIG. 11 with support member flexure.

FIG. 12 is an example embodiment of the delivery hose support 1000 of FIGS. 10 and 11 with flexure between lower distal portion 1008 and upper distal portion 1018 at living hinge 1030. With added reference to FIG. 13 expanded view 1300 of living hinge 1030 shows flexure at angle θ from axis 1310. It will be seen that a series of cuts 1320 are formed by a series of horizontal pairs of planar radial cuts that are separated by opposed, coplanar ribs 1330. Alternate planer cuts are rotated 90 degrees from one another providing axial flexure in all radial directions of support member 1012. Any suitable cut forming living hinge 1030 may be used.

Figure 15:
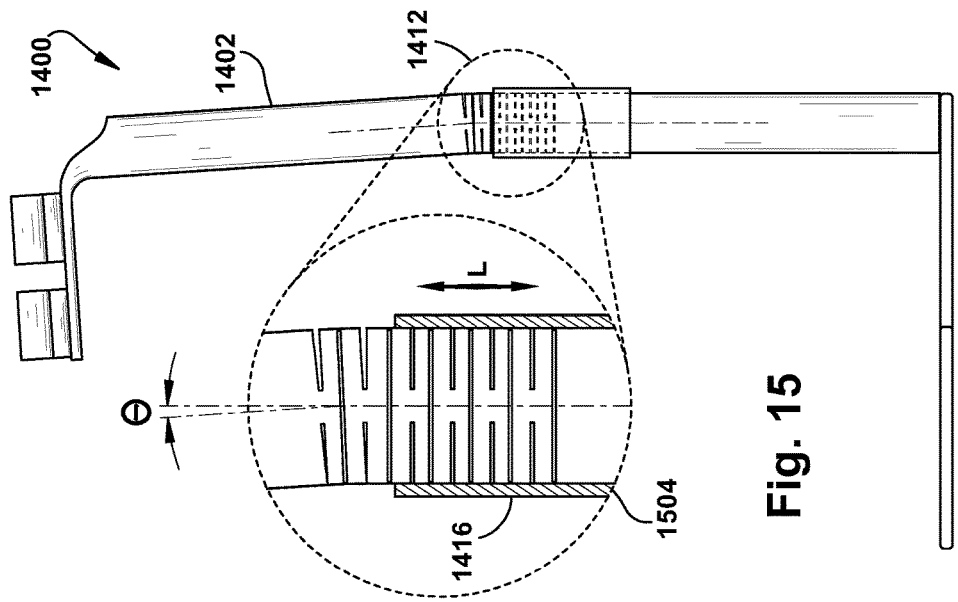
FIG. 15 is an example embodiment of a gas delivery hose support with an adjustable living hinge.
Figure 14:
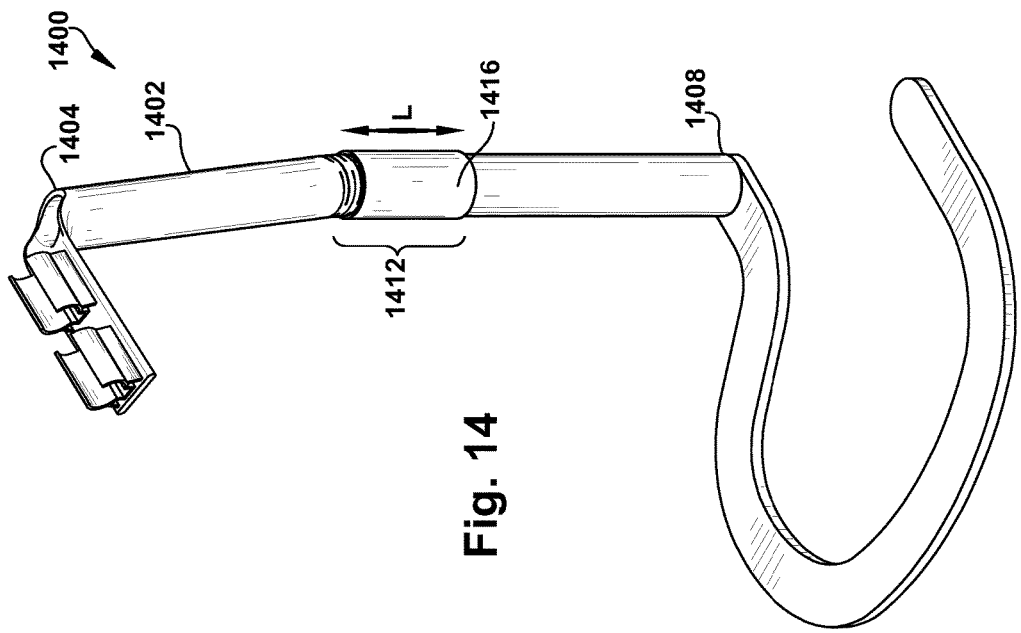
FIG. 14 is an example embodiment of a gas delivery hose support with and adjustable living hinge.

FIG. 14 is an example embodiment wherein hose support 1400 includes support member 1402 having upper distal end 1404 and lower distal end 1408. A living hinge 1412 is adjustable for tension or flexure by selective placement of a slide able sleeve 1416 that has a friction fit about an outer surface of support member 1402. With added reference to FIG. 15, living hinge 1412 is selectively coverable by sleeve 1416 by axial positioning L between sleeve 1416 and support member 1402. Such positioning results in different angles θ with application of the same force.

Figure 16A:
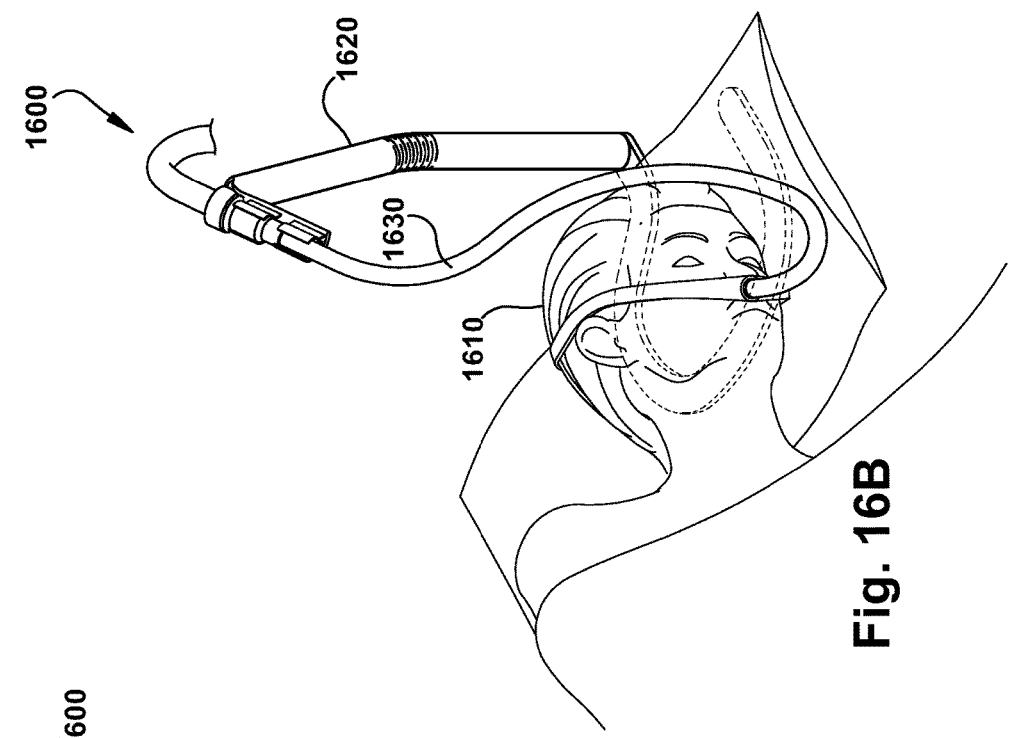
FIG. 16A is a second view of the gas delivery hose support of FIG. 15 showing flexure of the living hinge.
Figure 16B:
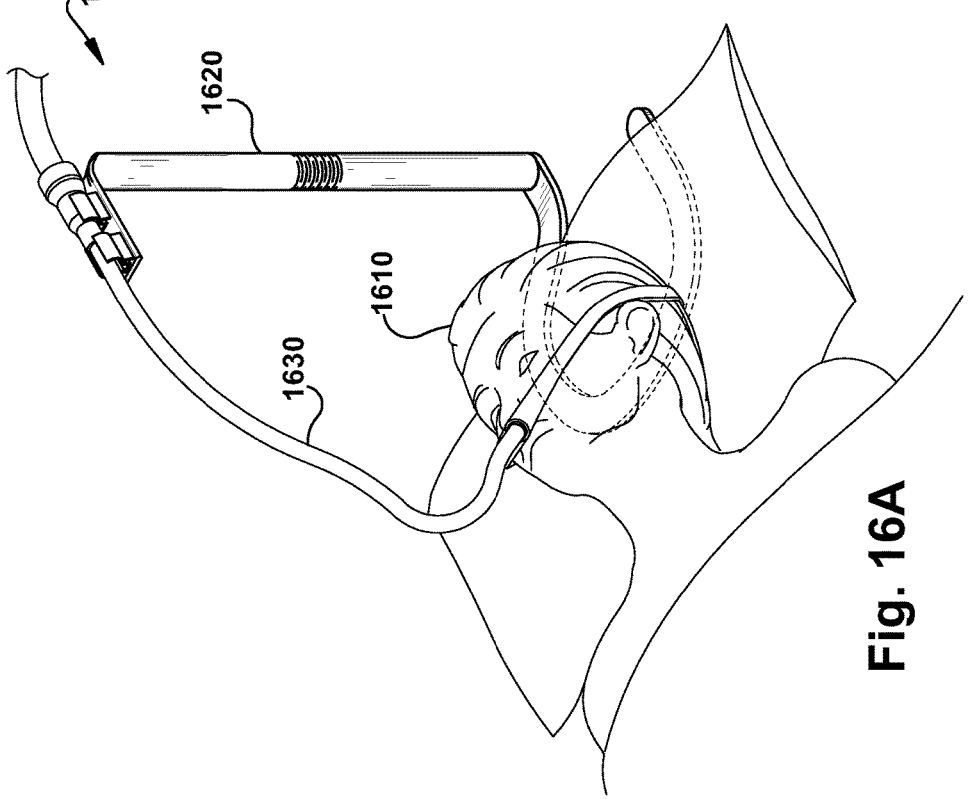
FIG. 16B is a second view of the gas delivery hose support of FIG. 15 showing flexure of the living hinge.

Referring next to FIGS. 16A and 16B, illustrated is hose support 1600 shown in situ with a device user 1610. In the illustration of FIG. 16A, device user 1610 is on their back and elongated member 1620 is under no substantive force from hose 1630 imparted from device user 1610. FIG. 16B illustrates device user 1610 on their side which imparts a force on to hose 1630 causing flexure and/or rotation of support member 1620.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the spirit and scope of the inventions.

What is claimed is:

1. A device comprising:
 a substantially rigid, elongated contiguous, tubular support member comprised of a tube wall having a first distal end, a second distal end, and a centralized living hinge biasing portion, integrated in the tube wall and comprised of a series of spaced apart slits in the tube wall, the living hinge, configured to bias arcuate movement between the first distal end and the second distal end, and wherein
 the living hinge has an axial length smaller than axial lengths of the first and second distal ends,
 a bias of the living hinge is configured to be adjustable while maintaining a fixed distance between the first and second distal ends, and
 the bias of the living hinge corresponds to a position of an outer tube disposed circumferentially along a surface of the tube so as to be slide-able relative to the biasing portion;
 a generally planar, rigid base configured to receive an associated pillow on an upper surface thereof so as to secure the first distal end so that the support member extends from a surface of the base to hold the first distal end in a generally vertical position relative to the second distal end when a radial force is applied to the second distal end during flexure of the living hinge;
 a mount comprised of first and second coaxial, biased C-clips secured to the second distal end, the mount configured to snap fit an associated tube thereto with substantially unrestricted fluid flow therethrough; and
 a mount support, formed from a cutaway portion of the tube wall, extending radially outwardly from the tube.

2. A system comprising:
 a substantially rigid planar base having a shaft projecting generally perpendicularly from a top surface thereof, the planar base configured to receive an associated pillow on an upper surface thereof;
 a tubular support member having first and second distal ends and an integrated, centralized living hinge, comprised of a plurality of spaced apart cuts through a wall of the support member disposed between the distal ends, wherein the living hinge has an axial length smaller than axial lengths of the first and second distal ends and wherein the support member is configured for rotational movement relative to the base when mated with the shaft when circumferential force is received by the mount from the gas delivery hose via first and second biased hose C-clamps;
 the support member configured to coaxially mate with the shaft at the first distal end so as to secure the first distal end in a generally vertical position relative to the second distal end when a radial force is applied to the second distal end during flexure of the living hinge;
 a mount extending radially from the second distal end; and
 a tubular adjustment sleeve having a frictional fit on an outer surface of the support wherein the sleeve is axially slidable relative to the support member and the living hinge such that a bias force of the living hinge varies relative to a position of the sleeve while maintaining a fixed distance between the first and second distal ends;

wherein the first and second coaxial biased hose C-clips are disposed on a surface of the mount and configured to snap fit to an associated gas delivery hose connected to the second distal end with substantially unrestricted fluid flow therethrough.

3. The system of claim 2 wherein the cuts are comprised of rectangular cuts.

4. The system of claim 2 wherein the cuts extend circumferentially about the support member.

5. The system of claim 2 wherein the base is curvilinear.

6. A device comprising:
an elongated support member comprised of a tube wall having a first distal end, a second distal end, and an adjustable living hinge biasing portion configured to adjustably bias arcuate movement between the first distal end and the second distal end, wherein the bias of the living hinge corresponds to a position of an outer tube disposed circumferentially along a surface of the tube so as to be slide-able relative to the biasing portion;

a generally planar, rigid base configured to secure the first distal end so that the support member extends from a surface of the base;

a mount secured to the second distal end, the mount configured to secure an associated tube thereto;

a mount support, formed from the tube wall, extending radially outwardly from the tube;

wherein the elongated support member is comprised of a tube and wherein the living hinge is integrated in a wall of the tube; and wherein the living hinge is comprise of a series of spaced apart slits in the tube wall.

* * * * *